(12) United States Patent
Woehr et al.

(10) Patent No.: US 8,529,515 B2
(45) Date of Patent: Sep. 10, 2013

(54) IV-CATHETER INSERTION DEVICE

(75) Inventors: Kevin Woehr, Felsberg (DE); Thomas Mueller, Bad Zwesten (DE)

(73) Assignee: B. Braun Melsungen AG, Melsungen (DE)

( * ) Notice: Subject to any disclaimer, the term of this patent is extended or adjusted under 35 U.S.C. 154(b) by 0 days.

(21) Appl. No.: 13/508,943

(22) PCT Filed: Nov. 12, 2010

(86) PCT No.: PCT/EP2010/006908
§ 371 (c)(1),
(2), (4) Date: Jul. 12, 2012

(87) PCT Pub. No.: WO2011/057802
PCT Pub. Date: May 19, 2011

(65) Prior Publication Data
US 2012/0277680 A1 Nov. 1, 2012

(30) Foreign Application Priority Data
Nov. 12, 2009 (DE) .......................... 10 2009 052 971

(51) Int. Cl.
*A61M 5/178* (2006.01)
(52) U.S. Cl.
USPC .................................... 604/164.08
(58) Field of Classification Search
USPC .................... 604/110, 164.08, 263
See application file for complete search history.

(56) References Cited

U.S. PATENT DOCUMENTS

| | | | |
|---|---|---|---|
| 4,944,725 A | 7/1990 | McDonald | |
| 5,215,525 A | 6/1993 | Sturman | |
| 5,853,393 A * | 12/1998 | Bogert | 604/165.02 |
| 6,117,108 A * | 9/2000 | Woehr et al. | 604/110 |
| 6,749,588 B1 | 6/2004 | Howell et al. | |
| 8,328,762 B2 * | 12/2012 | Woehr et al. | 604/164.08 |
| 2003/0199827 A1 * | 10/2003 | Thorne | 604/164.08 |
| 2006/0116638 A1 | 6/2006 | Woehr | |
| 2008/0132846 A1 * | 6/2008 | Shue et al. | 604/164.01 |
| 2012/0271235 A1 * | 10/2012 | Fuchs et al. | 604/164.08 |

FOREIGN PATENT DOCUMENTS

| | | |
|---|---|---|
| EP | 0 747 085 A2 | 12/1996 |
| FR | 2 835 754 A1 | 8/2003 |

OTHER PUBLICATIONS

International Search Report completed Apr. 27, 2011 and mailed May 4, 2011 from corresponding International Application No. PCT/EP2010/006908 filed Nov. 12, 2010 (4 pages).

* cited by examiner

*Primary Examiner* — Aarti B Berdichevsky
(74) *Attorney, Agent, or Firm* — Klein, O'Neill & Singh, LLP

(57) ABSTRACT

The present disclosure is directed to an IV-catheter insertion device, which comprises a catheter hub at the proximal end of a tubular catheter, a protective barrel releasably joined to the catheter hub in a ready position, a needle hub with an attached hollow needle, the hollow needle extending through the catheter hub and the tubular catheter in the ready position such that that needle tip projects distally of the distal end of the tubular catheter, wherein the needle hub is displaceable in the protective barrel, and a spring clip as a needle guard element whose proximal rear wall is fixed at a distal end area of the protective barrel by means of holding members, wherein the protective barrel and the catheter hub are held by the spring clip in the ready position, and the spring clip is released from the catheter hub in a protected position in which the spring clip covers the needle tip.

24 Claims, 7 Drawing Sheets

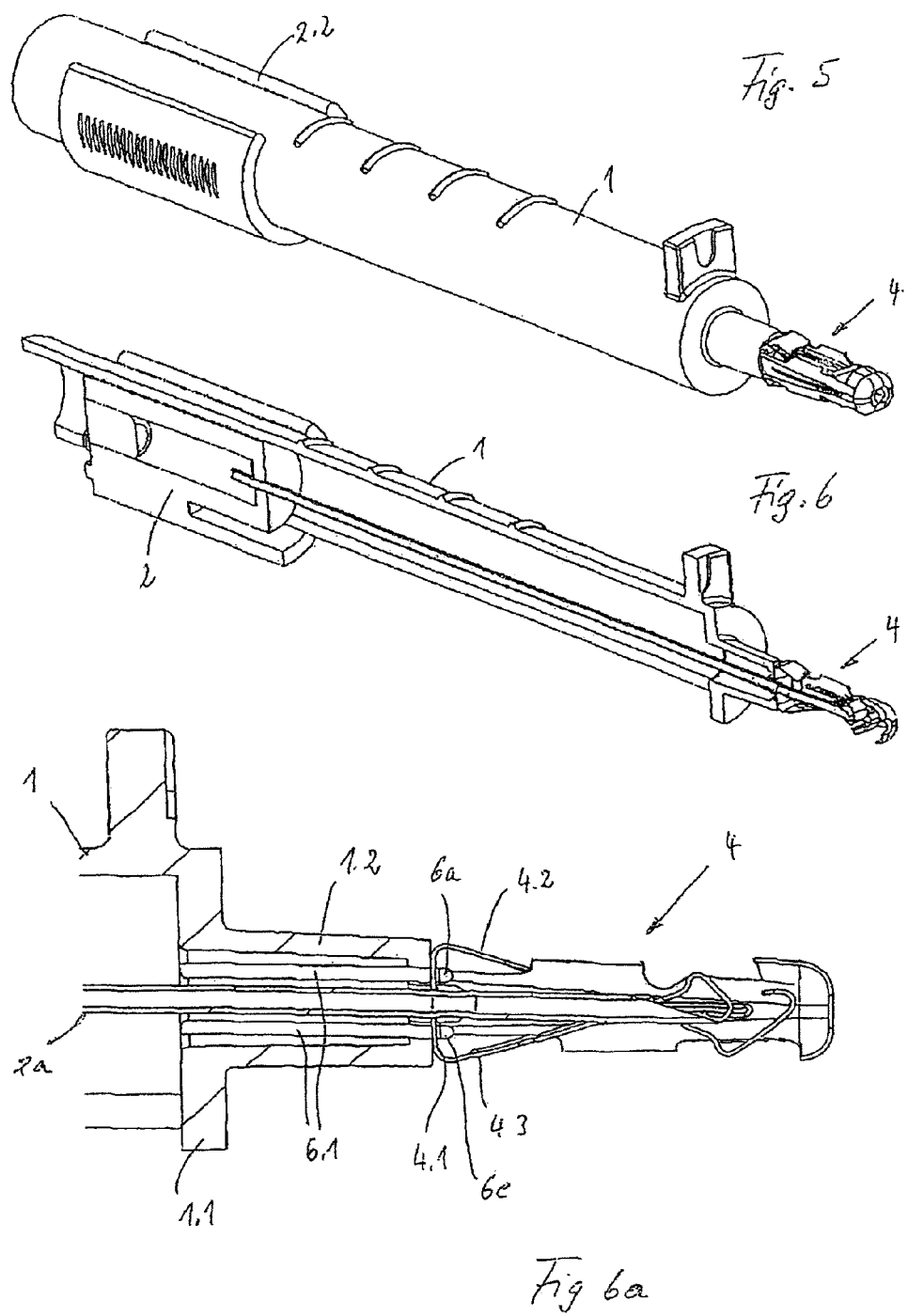

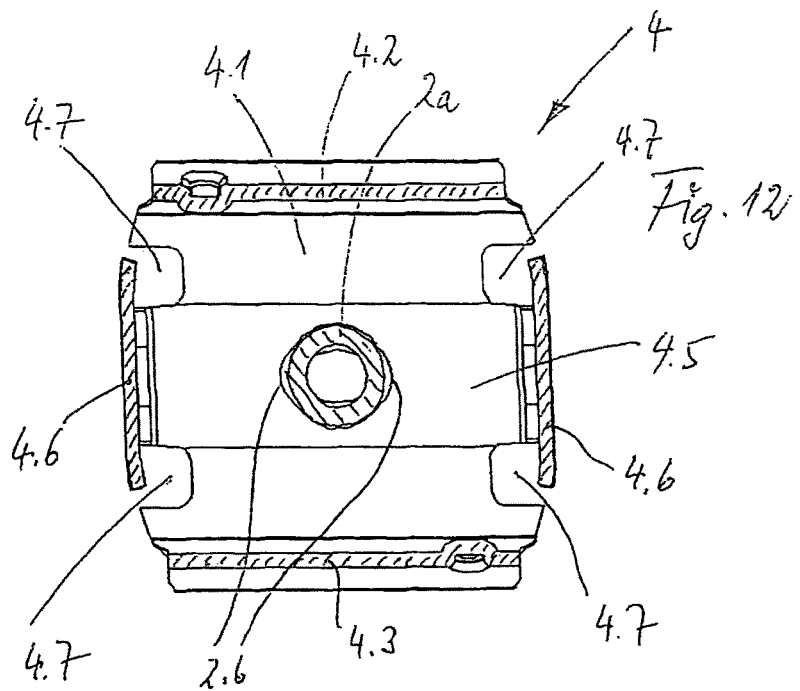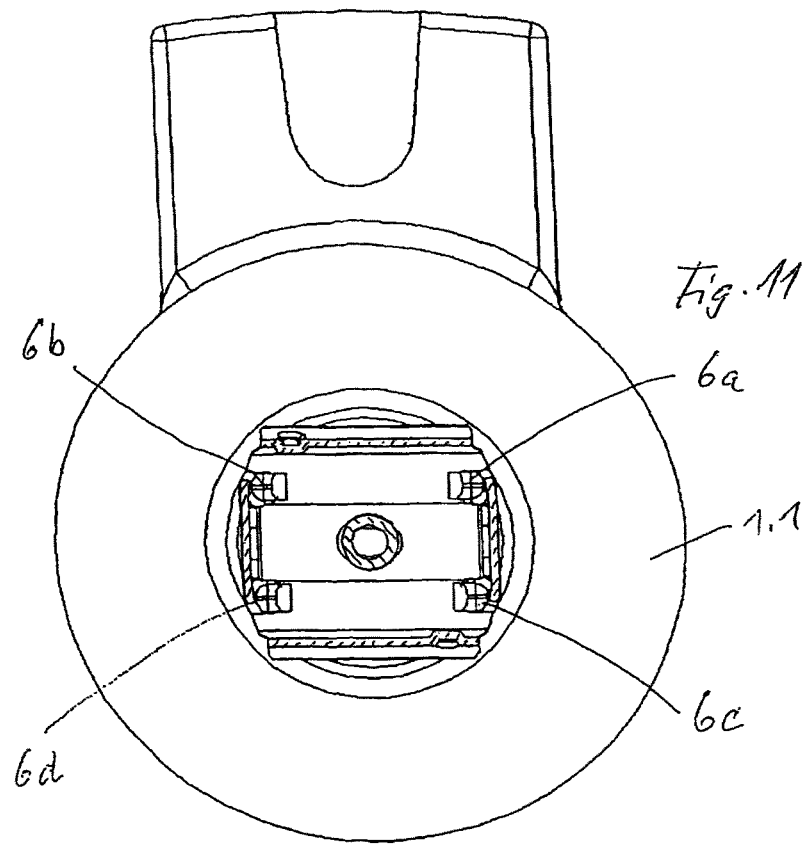

IV-CATHETER INSERTION DEVICE

CROSS-REFERENCE TO RELATED APPLICATIONS

This is a national phase application under 35 U.S.C. §371 of PCT Application No. PCT/EP2010/006908 filed Nov. 12, 2010, which claims the benefit of German application No. 10 2009 052 971.3 filed Nov. 12, 2009, the contents of each of which are expressly incorporated herein by reference.

FIELD OF ART

The present disclosure relates to an IV-catheter insertion device comprising a protective container or barrel attached releasably to the catheter hub of an IV-catheter including a catheter hub, a catheter tube and a hollow needle extending through the lumen of the catheter tube in the ready position whereby the hollow needle is received into the protective barrel in a protected position after the protective barrel is released from the catheter hub.

SUMMARY

In a preferred embodiment of the IV-catheter insertion device in according to the present disclosure, the device includes a needle hub which is displaceable in the protective barrel and also includes a spring clip which is affixed as a needle guard element to the distal end of the protective barrel by means of hooks, so that a spring clip which is otherwise usable for infusion needles and the like can also be used for an IV-catheter insertion device having a protective barrel.

Further aims, advantages, features and possible applications of the present method, system and device become apparent from the following description of the embodiments with reference to the drawing. Hereby, all the features described and/or shown diagrammatically form the subject matter of the present method, system and device, whether in themselves or in any meaningful combination, and independently of their summary in the claims and of the back-referencing of the claims.

BRIEF DESCRIPTION OF THE FIGURES

Examples of the present method, system and device are explained in more detail below with reference to the drawing, in which:

FIG. 5 shows a perspective view in the protected position, FIG. 6 shows a longitudinal section through the device in the protected position, FIG. 6*a* shows an enlarged representation in the protected position, FIG. 11 shows a front view of the protective barrel of FIG. 7 with a fourth modified embodiment of the spring clip represented in section, and FIG. 12 shows a sectional view of the spring clip of FIG. 11 and of the hollow needle without the protective barrel.

DETAILED DESCRIPTION

Figure 1:
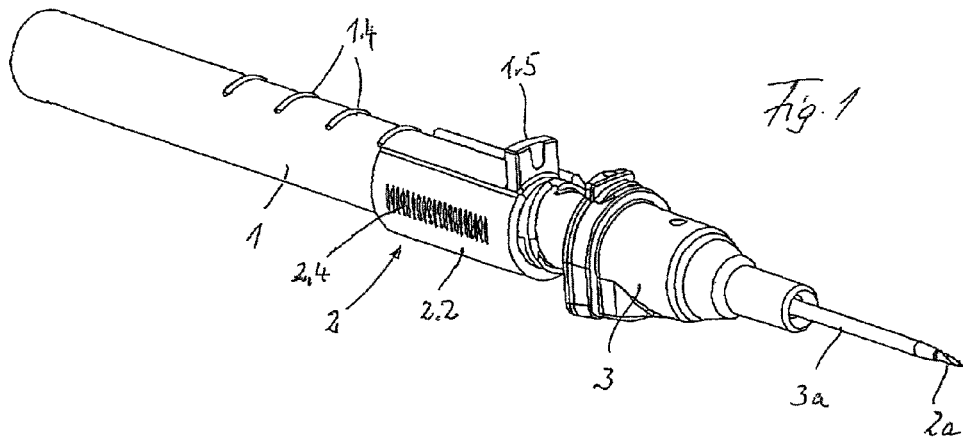
FIG. 1 shows a perspective view of an IV-catheter insertion device in the ready position.
Figure 2:
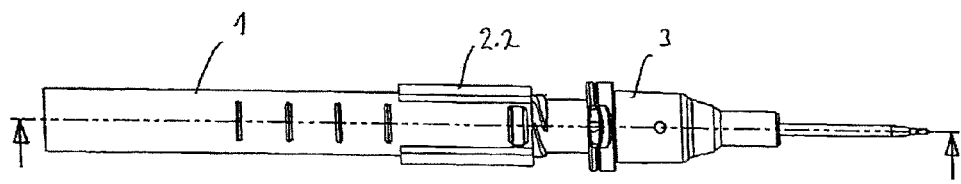
FIG. 2 shows a plan view of the device according to FIG. 1.

In the Figures, reference numeral 1 refers to a tubular protective barrel in which a needle hub 2 can be displaced, whereby the proximal end of a hollow needle 2*a* is attached to the needle hub, and the needle extends through a catheter hub 3 and a catheter tube 3*a* mounted thereon, wherein the tip of the needle 2*a* projects distally of the distal end of the catheter 3*a*.

Figure 3:
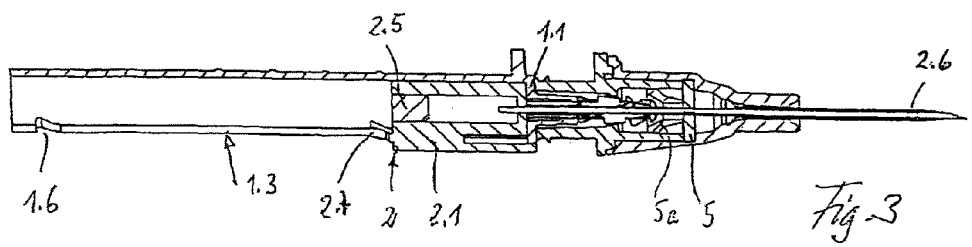
FIG. 3 shows a longitudinal section through the device in FIG. 2.
Figure 4:
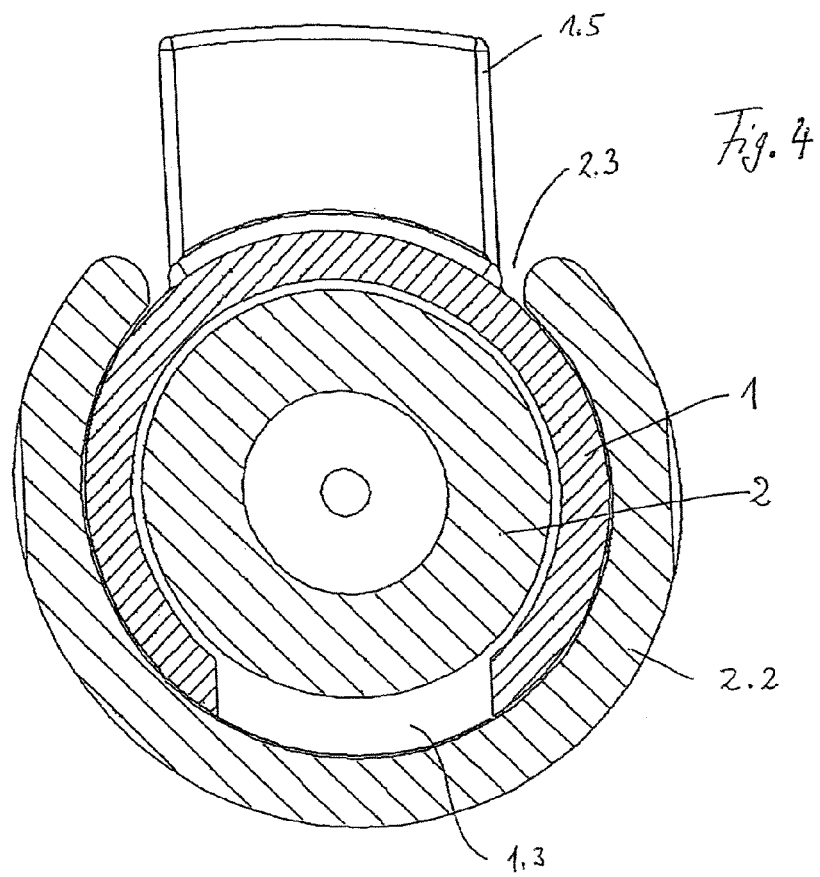
FIG. 4 shows a cross-section through the protective barrel and the needle hub with grip sleeve.

The tubular protective barrel 1 has a distal front wall 1.1 on which a distally projecting hub 1.2 is formed, in the embodiments according to FIGS. 3 and 5 to 7. In FIG. 3, on the underside of the protective barrel 1, there is a longitudinal slot 1.3 extending from the distal front wall 1.1 in a proximal direction, in which slot a radially projecting rib 2.1 of the needle hub 2 is displaceably guided, and a grip sleeve 2.2 extends from this radial rib in the distal direction and in the circumferential direction, wherein the grip sleeve is provided with a slot 2.3 extending continuously in the axial direction diametrically opposite the radial rib 2.1. FIG. 4 shows a cross-section through the protective barrel 1 and the needle hub 2, wherein the diametrically opposite longitudinal slot 1.3 of the protective barrel 1 and the slot 2.3 of the grip sleeve 2.2 of the needle hub 2 are to be seen. Ribs 2.4 are formed on the outside of the grip sleeve 2.2 and likewise on the upper side of the protective barrel 1 at reference numeral 1.4. Reference numeral 1.5 designates a radial lug at the protective barrel 1 for supporting the index finger during handling by an operator. The lug 1.5 and the ribs 1.4 are formed in the area of the longitudinal slot 2.3 of the grip sleeve 2.2, so that they do not hinder the displacement thereof along the outer circumference of the protective barrel 1.

Because the protective barrel 1 is open at the proximal end, in the embodiment represented the proximal end of the hollow cylindrical needle hub 2 is closed by a stopper 2.5 which catches blood. The blood-catching stopper is air-permeable but not blood-permeable.

Figure 3A:
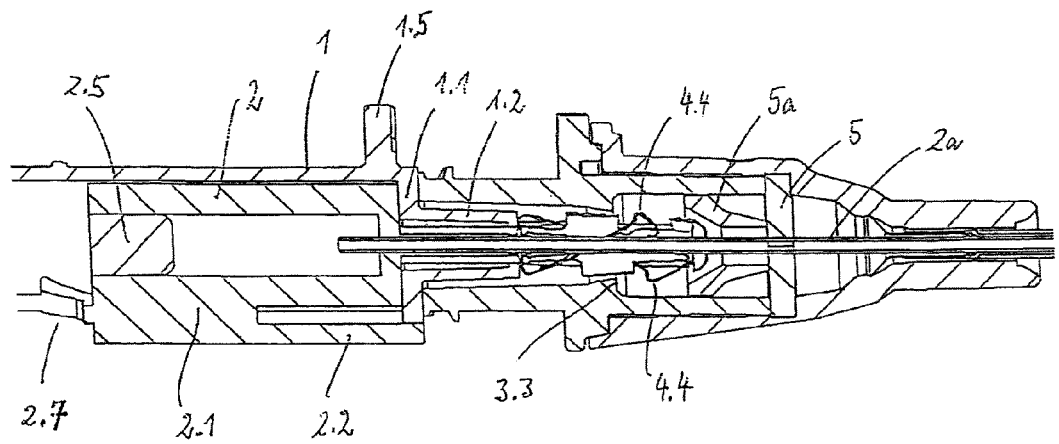
FIG. 3*a* shows an enlarged sectional view.

In the embodiment according to FIGS. 1 to 7, a spring clip 4 is connected to the distal hub 1.2 of the protective barrel 1, the protective barrel extending into the catheter hub 3 in the ready position, as shown in FIG. 3*a*. The spring clip has diametrically opposite spring arms 4.2 and 4.3 extending distally of a proximal rear wall 4.1 (FIG. 6*a*). The bent distal ends of the spring arms have radially-projecting elbow-shaped sections 4.4 which, during retraction of the needle hub and the needle 2*a* connected thereto from the catheter hub 3, come to rest in the catheter hub 3 at an annular shoulder 3.3 which projects radially inwards, so that the spring clip 4 is held in the catheter hub 3 at the annular shoulder 3.3 until the needle tip is positioned inside the spring clip 4 and the distal ends of the spring arms snap radially inwards to cover the needle tip, as FIGS. 6 and 6*a* show. The engagement of the spring clip 4 in the catheter hub 3 is thus released, and the protective barrel 1 can be released from the catheter hub 3 in the protected position shown in FIGS. 5 and 6 without any resistance.

In the embodiment shown, the spring arms 4.2 and 4.3 of the spring clip 4 are formed in a shape crossing each other. However, it is also possible to provide a spring clip whose spring arms extend approximately parallel to each other from the rear wall 4.1. A spring clip with one arm only can also be provided.

Further, in the embodiment of FIG. 3, a valve in the form of a valve disc 5 is provided in the catheter hub 3, which closes automatically when the needle 2a is retracted into the protected position. Reference numeral 5a designates a valve-actuation element which is distally displaced on insertion of a syringe or an infusion hose into the catheter hub to open the valve 5. For this, the valve-actuation element 5a preferably has at least one plunger (not shown here) which extends in axial direction to allow the direct abutment of a syringe neck or connecting piece at the valve-actuation element. Alternatively, however, the IV-catheter insertion device according to the present method, system and device can also be formed without any valve whatsoever or only with an automatic valve disc only (i.e. without any valve-actuation element).

Near the needle tip, a crimp formed by a needle crimp, or an alternately formed radial projection 2.1, is shown (FIG. 3) which, in the protected position in FIG. 6a, comes to rest at the proximal rear wall 4.1 of the spring clip 4 and thereby also holds the needle hub 2 via the needle 2a on the protective barrel 1 in the position shown in FIG. 6.

Moreover, lugs 2.7 are formed at the proximal end of the needle hub 2 (FIG. 3), which engage in a notch 1.6 at the proximal end of the protective barrel 1 at the opposite edges of the longitudinal slot 1.3, when the needle hub 2 is displaced into the protected position in proximal direction in relation to the protective barrel 1. However, the needle hub can alternatively be held only by the crimp 2.1, without lugs 2.7 having to be provided. However, it is also possible to form the needle without a crimp, so that the needle hub is then held only by the engagement of the lugs 2.7 in the notch 1.6.

Thus, in addition to the protective function in relation to the needle tip, the needle guard element in the form of the spring clip 4 fixed to the protective barrel 1 also fulfils two holding functions the first between the catheter hub 3 and the protective barrel 1 and the second between the protective barrel 1 and the needle hub 2. In the ready position of FIG. 3, the spring clip 4 holds the protective barrel 1 abutting at the catheter hub 3 as long as the elbows 4.4 at the distal wall portions of the spring clip 4 engage behind the annular shoulder 3.3 in the catheter hub. This engagement prevents the axial disconnection of the catheter hub 3 from the protective barrel 1 in the ready position, so that the catheter hub 3 and the protective barrel 1 together with the needle hub 2 form a unit. In the protected position of FIGS. 5 and 6, the spring clip 4 holds the needle hub 2 at the protective barrel 1 against displacement in proximal direction by engagement of the edge of the bore in the proximal rear wall 4.1 of the spring clip with the projection 2.1 at the needle 2a, so that no further holding means are required between the proximal end of the protective barrel 1 and of the needle hub 2, as shown at 1.6 and 2.7, in order for the protective barrel 1 and the needle hub 2 to form a unit for disposal.

Figure 7:
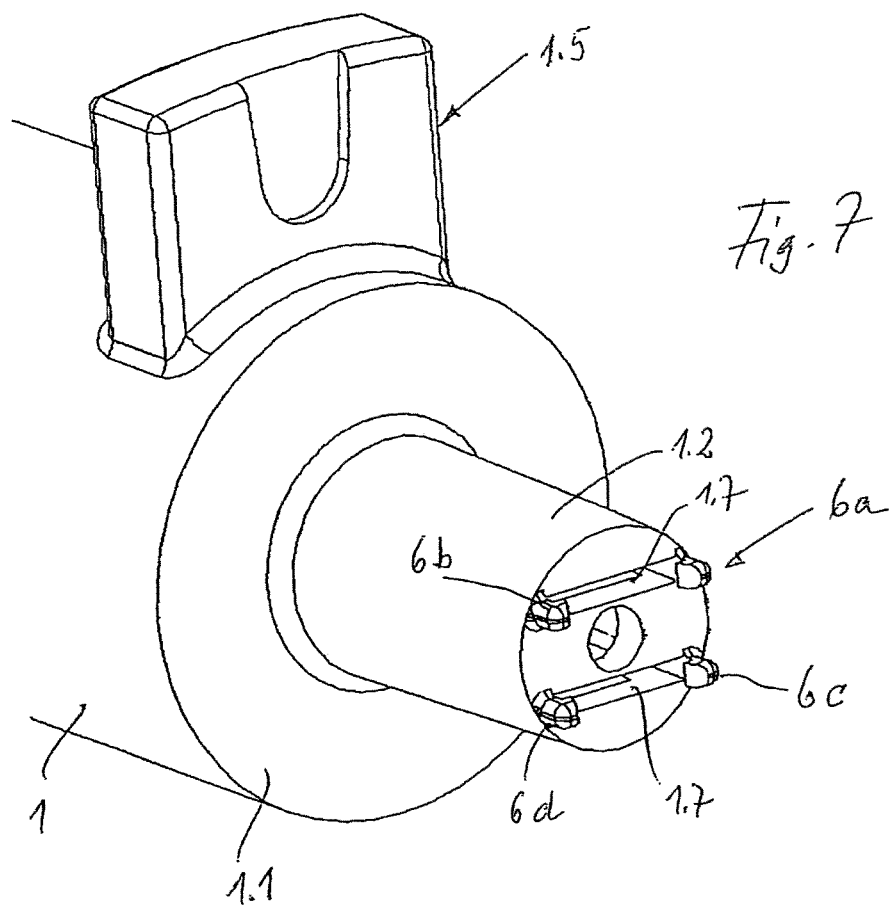
FIG. 7 shows a perspective view of the distal end of the protective barrel without spring clip.

FIG. 7 shows holding members for the spring clip in the form of four hooks 6a to 6d at the distal front side of the hub 1.2 of the protective barrel 1, which hooks are positioned pair-wise opposite each other and engage the approximately rectangular proximal rear wall 4.1 of the spring clip 4 at the opposite side edges, as FIG. 6a shows.

In the embodiment of FIG. 7, the hooks 6a, 6b and 6c, 6d are formed at the ends of each slot 1.7 in the front wall of the hub 1.2 in order to facilitate manufacture, for example by injection moulding, when the hooks 6 on the protective barrel 1 are to be released from the moulding form. The two slots 1.7 extend on both sides of a throughhole in the front wall 1.1 through which the needle extends, wherein FIG. 6a shows grooves 6.1 on the inner circumference of the hollow hub 1.2 which extend from the hooks 6 and serve for easier deformation of the protective barrel during the manufacture thereof.

Figure 8:
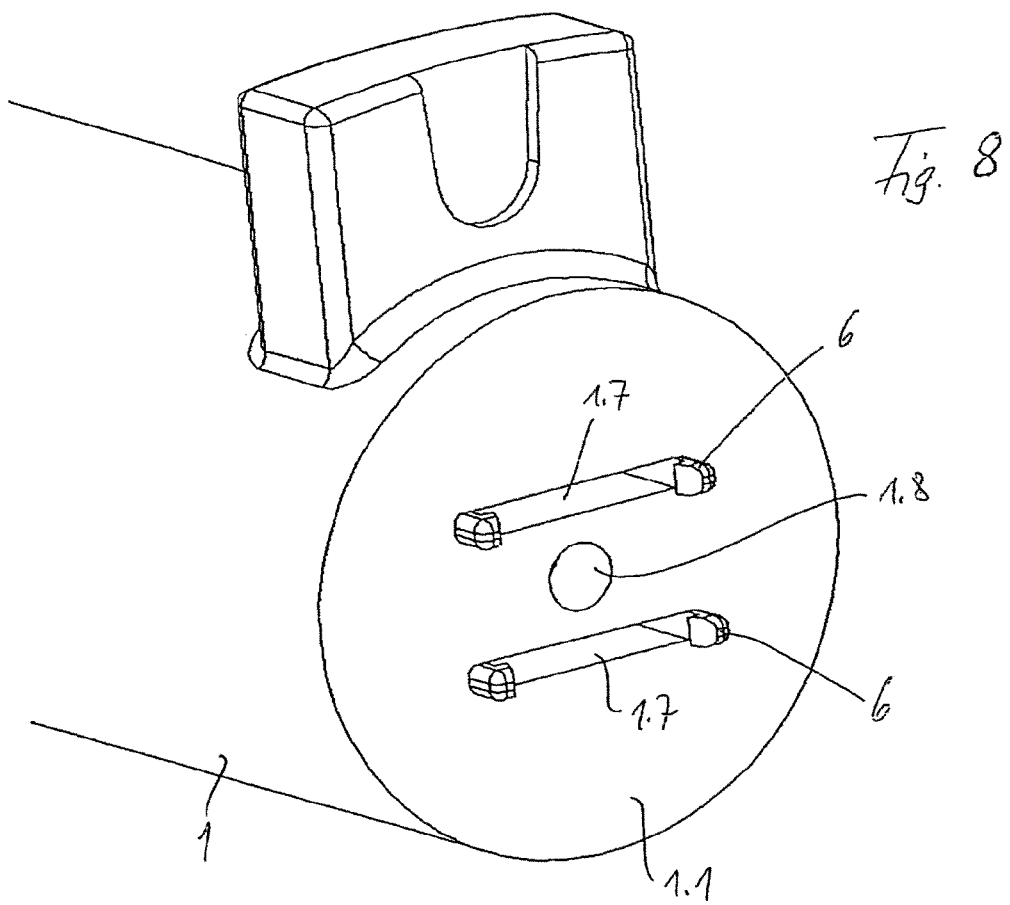
FIG. 8 shows a further embodiment of the protective barrel in the same view.

FIG. 8 shows an embodiment in which the hooks 6 are formed in the same way as in FIG. 7, but are formed directly on the front side 1.1 of the protective barrel 1.

Figure 9:
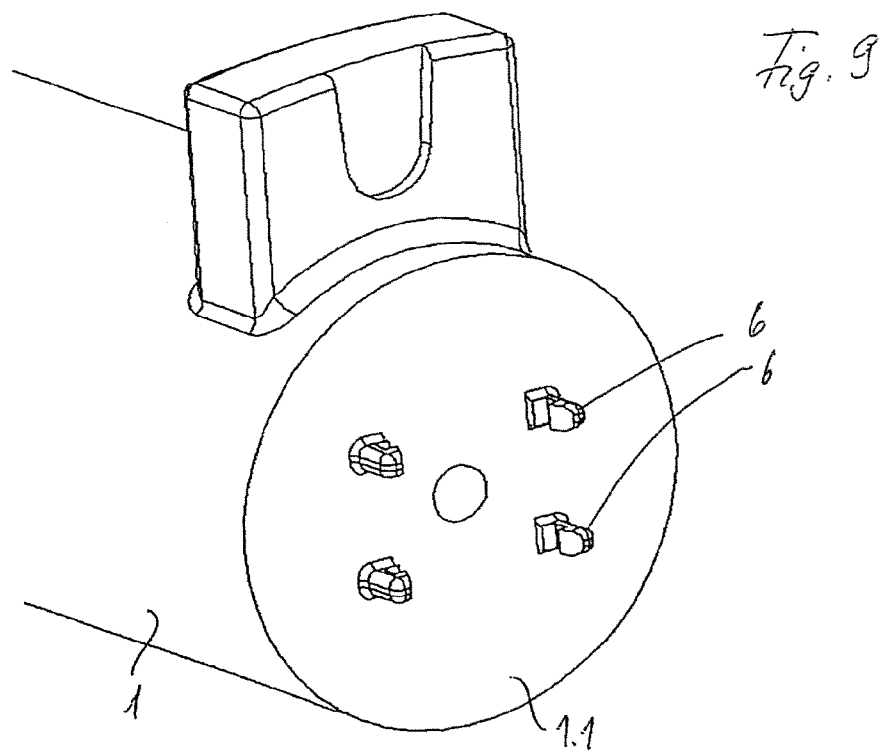
FIG. 9 shows a second modified embodiment in the same view.

In the embodiment of FIG. 9, the hooks 6 are formed on the front side 1.1 of the protective barrel 1 without a slot being formed in the front wall 1.1 between the opposite hooks 6a, 6b and 6c, 6d. The embodiment according to FIG. 7 can likewise be formed without a slot 1.7 and groove 6.1. Instead of two slots 1.7, four holes (not shown) behind the four hooks can likewise facilitate deformation without weakening the front wall, when the protective barrel 1 is released from the moulding form.

Figure 10:
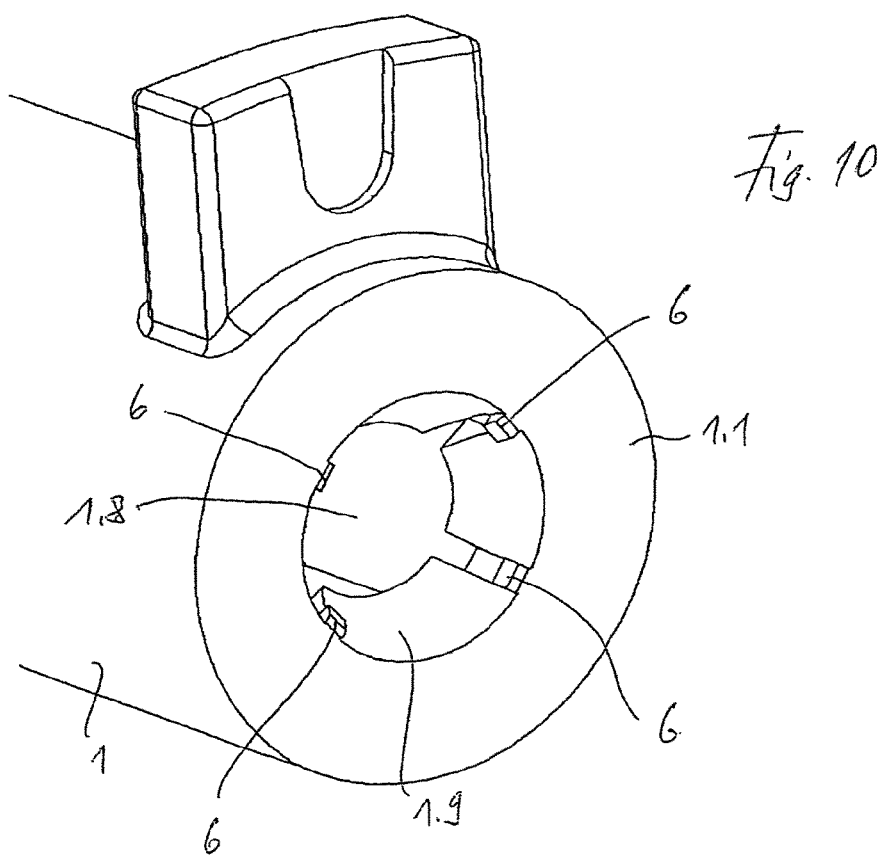
FIG. 10 shows a third modified embodiment in the same view.

FIG. 10 shows an embodiment in which the front wall 1.1 of the protective barrel 1 has an approximately funnel-shaped middle recess 1.8 whose diameter in the area of the plane of the front wall 1.1 is larger than the radial dimension of the proximal rear wall 4.1 of the spring clip 4, so that this spring clip can be partly inserted in this recess 1.8. At the side wall 1.9 of the recess 1.8, slots are formed extending in the axial direction, in which slots the hooks 6 are formed projecting radially inwards.

In the embodiment of FIG. 10, the hooks 6 are formed such that their distal end is substantially aligned with the front surface 1.1 of the protective barrel 1, so that the engagement part of the hooks extends inwards into the recess 1.8. However, it is also possible to form the hooks 6 deeper in the recess 1.8 in the axial direction, in order to hold the proximal rear wall 4.1 of the spring clip in the recess 1.8. In any case, the arrangement of the hooks 6 in the recess 1.8 is provided such that the spring arms 4.2 and 4.3 of the spring clip are not biased too much in the recess 1.8 of the protective barrel 1.

In the embodiment shown in FIG. 10, the recess 1.8 is provided with a larger opening at the inner end. It is also possible to form only a throughhole for the needle at the inner area of the recess 1.8. However, such a smaller throughhole is not advantageous to the manufacturing of the protective barrel 1 by injection moulding.

The advantage of the embodiments in FIGS. 8-10 is that the four hooks can be arranged further apart from each other. What is disadvantageous is that the spring clip must be longer in order to engage the annular shoulder 3.3 in the catheter hub.

Instead of the hooks 6, other embodiments of holding members can also be formed as holding members for the spring clip at the front side of the protective barrel 1. For example, mushroom-shaped pins can be provided which engage in holes in the proximal wall of the spring clip and/or are joined to the spring clip by bonding, riveting or welding.

The spring clip used is preferably the spring clip 4 described in DE 10 2009 020 061, represented in FIGS. 3 and 6 in longitudinal section and in FIG. 5 in a perspective view.

FIGS. 11 and 12 show a cross-section through the spring arms 4.2 and 4.3 and through the side walls 4.6 with a view of the proximal rear wall 4.1. In this embodiment of the spring clip, the side edges of the proximal rear wall 4.1 lie too far apart from each other for engagement of the hooks 6, for which reason lateral cut-outs 4.7 are provided at the proximal rear wall 4.1, as FIG. 12 shows, in which the hooks 6 engage, as FIG. 11 shows. In FIG. 12, 4.5 designates a ridge, which is embossed in the proximal rear wall 4.1 of the spring clip, and extends between the two side walls 4.6. FIG. 11 corresponds to the protective barrel 1 in FIG. 7, with the spring clip 4 held at the hooks 6, corresponding to FIG. 6a. Because the distally projecting hub 1.2 engages in the standard Luer cone of the catheter hub 3, there is not enough space to position the hooks outside the proximal rear wall 4.1. Therefore, the cut-outs 4.7 are provided.

When the hooks 6 are arranged in the protective barrel 1 (FIGS. 8 and 9), the hooks 6 can be applied directly at the proximal rear wall 4.1 of the spring clip 4 in order to hold it, without cut-outs 4.7 being provided. As already mentioned, in this case the spring clip must be of longer length in order to be able to engage behind the annular shoulder 3.3 in the catheter hub.

When the hooks 6 are arranged in the recess 1.8 of the protective barrel 1 (FIG. 10) and the hooks 6 are arranged on a circular circumference and directed to the centre point of the circle, radially projecting lugs can be provided at the proximal rear wall 4.1 of the spring clip 4, at which the hooks 6 in FIG. 10 engage for holding the spring clip 4.

This shorter configuration of the needle hub 2 in relation to the protective barrel, leads to a shorter configuration in the protected position in which the needle hub and the needle are substantially received in the protective barrel.

Various modifications of the described type of construction are possible. For example, a spring can also be provided between the distal front side of the needle hub 2 and the front wall 1.1 of the protective barrel 1 in connection with a triggering mechanism for the spring, so that instead of manual operation by backward displacement of the grip sleeve 2.2, the displacement of the needle hub into the protected position can be achieved by spring action. In such an embodiment, the grip sleeve 2.2 can be omitted.

Further the spring clip 4 can be embodied as another kind of needle guard element. Needle guard elements as shown in WO 99/08742 can be used. Further it is also possible that a sleeve having a rear wall can be used as needle guard element wherein the distal end of the sleeve has radial elasticity by slits which extend parallel to the axis of the sleeve on the distal end which can be provided by an engagement means on the outer circumference for engaging the inner circumference of the catheter hub.

The needle guard element can be made of metal and/or plastic material and can comprise several parts.

The invention claimed is:

1. An IV-catheter insertion device, comprising:
   a catheter hub at a proximal end of a tubular catheter,
   a rigid protective barrel formed by moulding releasably joined to the catheter hub in a ready position;
   a needle hub with an attached hollow needle having a needle tip, the hollow needle extending through the catheter hub and the tubular catheter in the ready position such that the needle tip projects distally of a distal end of the tubular catheter, wherein the hollow needle is displaceable in a protective barrel; and
   a needle guard element having a proximal rear wall held at a distal end area of the protective barrel by one or more holding members;
   wherein the protective barrel and the catheter hub are held by the needle guard element in the ready position, and the needle guard element is released from the catheter hub in a protected position in which the needle guard element covers the needle tip.

2. The IV-catheter insertion device according to claim 1, wherein the protective barrel is tubular in configuration in the ready position.

3. The IV-catheter insertion device according to claim 1, further comprising a projecting hub located inside the catheter hub in the ready position.

4. The IV-catheter insertion device according to claim 1, wherein the needle guard element comprises an arm that springs in the protected position.

5. The IV-catheter insertion device according to claim 1, wherein the hollow needle comprises a round outer contour along a length of the hollow needle and a non-round deformed outer contour near the needle tip.

6. The IV-catheter insertion device according to claim 1, wherein the one or more holding members are hooks for holding the needle guard element at the distal end area of the protective barrel.

7. The IV-catheter insertion device according to claim 6, wherein the one or more holding members are hooks on the distal end area of the protective barrel.

8. The IV-catheter insertion device according to claim 1, wherein a longitudinal slot formed in the protective barrel guides a radial rib connected to a grip sleeve, which extends around an outer circumference of the protective barrel.

9. The IV-catheter insertion device according to claim 8, wherein the grip sleeve has a longitudinal slot.

10. The IV-catheter insertion device according to claim 1, wherein the protective barrel and the needle hub move relative to one another in moving to the protected position.

11. The IV-catheter insertion device according to claim 10, wherein the needle guard element has a metallic wall surface that blocks the needle tip in the protected position.

12. The IV-catheter insertion device according to claim 10 wherein the hollow needle is covered by both the protective barrel and the needle guard element in the protected position.

13. An IV-catheter insertion device, comprising:
   a catheter hub comprising an interior cavity and having a tubular catheter attached thereto;
   an elongated tubular protective barrel releasably joined to the catheter hub in a ready position;
   a needle hub with an attached hollow needle having a needle shaft and a needle tip, the hollow needle extending through the catheter hub and the tubular catheter in the ready position such that the needle tip projects distally of a distal end of the tubular catheter, wherein the needle is displaceable in the tubular protective barrel and the needle hub is movable relative to the tubular protective barrel; and
   a needle guard element having a proximal rear wall held at a distal end area of the tubular protective barrel by one or more holding members;
   wherein the tubular protective barrel is removably fixed to the catheter hub until the needle guard element is released from the catheter hub in a protected position in which the needle guard element then covers the needle tip and the tubular protective barrel surrounds the needle shaft.

14. An IV-catheter insertion device according to claim 13, wherein the one or more holding members are hooks for holding the needle guard element at the distal end area of the protective barrel.

15. The IV-catheter insertion device according to claim 13, wherein the needle guard element has a metallic wall surface that blocks the needle tip in the protected position.

16. The IV-catheter insertion device according to claim 13, wherein needle is covered by both the protective barrel and the needle guard element in the protected position.

17. The IV-catheter insertion device according to claim 13, wherein the tubular protective barrel is rigid and formed by moulding.

18. The IV-catheter insertion device according to claim 13, wherein the one or more holding members are hooks on a distal end of the tubular protective barrel.

19. The IV-catheter insertion device according to claim 18, wherein the needle guard element has cut-outs at a proximal rear wall for engaging the hooks.

20. An IV-catheter insertion device, comprising:
a catheter hub comprising an interior cavity and having a tubular catheter attached thereto;
an elongated protective barrel releasably joined to the catheter hub in a ready position;
a needle hub with an attached hollow needle having a needle shaft and a needle tip, the hollow needle extending through the catheter hub and the tubular catheter in the ready position such that the needle tip projects distally of a distal end of the tubular catheter, wherein the hollow needle is displaceable in the protective barrel and the needle hub is movable relative to the protective barrel; and
a needle guard element having a proximal rear wall retained at the distal end area of the protective barrel by one or more holding members; and
wherein the needle guard element moves from the ready position where the needle guard element has a metallic spring clip having a first dimension of a first size to a protected position where the needle guard element covers the needle tip of the hollow needle and the metallic spring clip has a second dimension of a second size to cover the needle tip.

21. The IV-catheter insertion device according to claim 20, wherein the holding members are hooks for holding the protective barrel and the needle guard element together.

22. An IV-catheter insertion device according to claim 20, wherein the metallic spring clip comprises an arm that springs in the protected position.

23. The IV-catheter insertion device according to claim 20, wherein the protective barrel and the needle hub move relative to one another in moving to the protected position.

24. The IV-catheter insertion device according to claim 20, wherein the needle shaft comprises a round outer contour along a length of the needle shaft and a non-round deformed outer contour near the needle tip.

* * * * *

UNITED STATES PATENT AND TRADEMARK OFFICE
CERTIFICATE OF CORRECTION

PATENT NO. : 8,529,515 B2  
APPLICATION NO. : 13/508943  
DATED : September 10, 2013  
INVENTOR(S) : Woehr et al.

Page 1 of 1

It is certified that error appears in the above-identified patent and that said Letters Patent is hereby corrected as shown below:

On the Title Page,

Column 2, line 2, item [57] abstract, delete "comprises" and insert -- has --, therefor.

Column 2, line 7, item [57] abstract, delete "that that" and insert -- that the --, therefor.

In the Claims,

Column 6, line 39, claim 13, delete "the" and insert -- the hollow --, therefor.

Column 7, line 17, claim 20, delete "the" and insert -- a --, therefor.

Signed and Sealed this
Fourth Day of November, 2014

Michelle K. Lee
*Deputy Director of the United States Patent and Trademark Office*